United States Patent [19]
Humbert et al.

[11] 3,971,798
[45] July 27, 1976

[54] PYRIDINE DERIVATIVE, PROCESSES OF PREPARATION AND PHARMACEUTICAL COMPOSITIONS

[75] Inventors: Daniel Humbert, Paris; Roger Ratouis, Saint-Cloud, both of France

[73] Assignee: Roussel-UCLAF, Paris, France

[22] Filed: July 2, 1974

[21] Appl. No.: 485,244

[30] Foreign Application Priority Data
July 5, 1973    France .............................. 73.24737

[52] U.S. Cl. ......................................... 260/295 CA
[51] Int. Cl.² ....................................... C07D 213/24
[58] Field of Search ............................. 260/295 CA

[56] References Cited
UNITED STATES PATENTS
3,369,025   2/1968   Bolhofer ........................... 260/295

FOREIGN PATENTS OR APPLICATIONS
4,430,271   6/1969   Japan ........................... 260/295 CA
4,531,185   8/1970   Japan ........................... 260/295 CA
4,539,265   10/1970  Japan ........................... 260/295 CA OTHER PUBLICATIONS
Migrdichian, Organic Synthesis, vol. 1 (1957) p. 449.

*Primary Examiner*—Norman A. Drezin
*Attorney, Agent, or Firm*—Bacon & Thomas

[57]     ABSTRACT

There are provided 2-(p-chlorophenoxy) 2,2-dimethylacetate of 6'-(N-methylaminocarbonyloxymethyl) 2'-pyridyl/ methyl and its acid addition salts which have pharmacological properties particularly for regularizing metabolism, normalizing coagulation factors, combatting arteriosclerosis, chronic veinous insufficiencies and arterial hypertension. Also provided is a process for preparation of the compounds.

3 Claims, No Drawings

PYRIDINE DERIVATIVE, PROCESSES OF PREPARATION AND PHARMACEUTICAL COMPOSITIONS

BACKGROUND OF THE INVENTION

1. Field of the Invention

This invention relates to a novel free base and its acid addition salts, their methods of preparation and methods for use in therapeutic areas.

2. Description of the Prior Art

Various pyridine derivatives are known in the prior art, some of which have pharmacologically useful properties. For example, French Medicament Pat. No. 5814 M (Merck) discloses the phenoxy dimethylacetate of 3-pyridine methanol. The present invention however provides a new pyridine derivative which has new and useful pharmacological properties.

DESCRIPTION OF THE INVENTION

The present invention provides the new compound, 2-(p-chlorophenoxy) 2,2-dimethylacetate of /6'-(N-methylaminocarbonyloxymethyl) 2'-pyridyl/ methyl and the salts of addition with an organic or mineral acid. For use in pharmaceutical areas, the non-toxic addition salts are contemplated.

The basic compound of this invention, the 2-(p-chlorophenoxy) 2,2-dimethylacetate of 6'-(N-methylaminocarbonyloxymethyl) 2'-pyridyl methyl may also be named as 2-(2-p-chlorophenoxy) 2,2-dimethylacetoxymethyl) 6-(N-methylaminocarbonyloxymethyl) pyridine. In its free base form, the compound has the following structural formula:

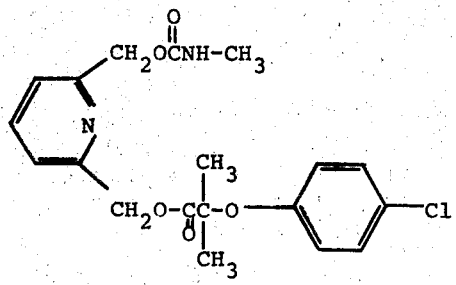

Also covered by the invention are the acid addition salts of the free base compound. The addition salts include, for example, those obtained by reaction with hydrochloric acid, hydrobromic acid, hydroiodic acid, nitric acid, sulfuric acid, phosphoric acid, acetic acid, maleic acid, furmaric acid, succinic acid, tartaric acid, citric acid, benzoic acid, alkylsulfonic acid and cyclohexylsulfamic acid. Among these salts, particularly preferred is the 2-(p-chlorophenoxy) 2,2-dimethylacetate of /6'-(N-methylaminocarbonyloxymethyl) 2'-pyridyl/methane hydrochloride.

The invention also provides a process for the preparation of the 2-(p-chlorophenoxy) 2,2-dimethylacetate of 6'-(N-methylaminocarbonyloxymethyl) 2'-pyridyl methyl, and the salts of addition with a mineral or organic acid, characterized in the reaction of the chloride of the p-chlorophenoxyisobutyric acid with 2,6-pyridine bis-methanol (2,6-dihydroxymethyl pyridine), obtaining the resulting 2-(p-chlorophenoxy) 2,2-dimethyl acetate of 6'-(hydroxymethyl) 2'-pyridyl methyl, and then reacting with an methyl isocyanate to obtain the 2-(p-chlorophenoxy) 2,2-dimethylacetate of 6'-(N-methylaminocarbonyloxymethyl) 2'-pyridyl methyl. To form the addition salts, the free base is reacted with the desired organic or mineral acid.

The invention also provides a process for the preparation of the novel product. In the preferred embodiment of the process of the invention, a condensation reaction between the chloride of the p-chlorophenoxyisobutyric acid and 2,6-pyridine bis-methanol is carried out in the presence of an organic solvent for the reactants. The solvent may be anhydrous but it is not a requirement. Preferred solvents include lower alkyl alcohols and lower alkyl ketones, preferably ethanol and acetone.

In conducting the reaction, it is preferred to dissolve the 2,6-pyridine bis-methanol in an excess of solvent and adding the acid chloride thereto at a temperature of about −5°C. to +5°C. After the addition is complete, the mixture is maintained at room temperature (20°–35°C.) for 12–36 hours to complete the reaction. On removal of excess solvent, the product is recovered.

The product from this reaction, 2-(p-chlorophenoxy) 2,2-dimethyl acetate of 6'-(hydroxymethyl)-2'-pyridyl methyl which may also be named as 2-(p-chlorophenoxy) 2,2-dimethylacetoxymethyl-6-hydroxymethyl-pyridine, is then reacted stoichiometrically with the methyl isocyanate. This reaction takes place in a solution of an aliphatic or cyclic ether, such as for example, ethyl ether or tetrahydrofuran. The methyl isocyanate is added a little at a time or portionwise with agitation of the mixture at temperatures ranging from −15°C. to 0°C. The reaction is completed by refluxing the mixture for 5–10 hours after which the solvent and excess isocyanate are removed. Thereafter, the mixture is acidified at −10°C. to 0°C., maintained at that temperature for 40–60 hours and the product recovered.

The acid addition salts of the free base resulting from this reaction are formed by reaction with a stoichiometric amount of the desired organic or mineral acid in an organic solvent solution, preferred solvents being alkyl ethers such as ethyl ether, lower alkyl alcohols such as ethanol or lower alkyl ketones such as acetone. The reaction will proceed at room temperature and the product is recovered on solvent removal.

The products of the present invention have been found to have interesting and useful pharmacological properties, particularly in that the products exhibit excellent hypolipemia activity and a strong anti-bradykinine effect. These properties make the products of the invention useful in various therapeutic areas such as permitting regularizing of the metabolism of lipids in the blood, normalizing the coagulation factors in the blood during the course of hyperlipidemia, combatting arteriosclerosis, atheromatosis, chronic veinous insufficiencies and arterial hypertension. Thus the products find utility in a number of areas involving the blood.

The products of the invention are administered by oral, rectal or subcutaneous methods. They can be presented in the form of tablets, cachets, pills, emulsions, syrups, solutions, suppositories and injectable suspensions, the preparation of which are well known to the art.

The invention also concerns pharmaceutical compositions comprising as the active principal the products of the invention as well as methods for administering the pharmaceutical compositions. These pharmaceutical compositions are prepared according to usual techniques known to the pharmaceutical industry.

The dosage amount can vary according to the subject or host, the manner of administration and the illness treated. For example, 1 to 5 grams per day by oral administration for an adult is satisfactory.

The following examples are illustrative of the invention without in any way limiting the same. In the examples and throughout the specification, parts are by weight unless otherwise indicated.

EXAMPLE I

Hydrochloride of 2-(p-chlorophenoxy) 2,2-dimethylacetate 6-(N-methylaminocarbonyloxymethyl) 2'-pyridyl methyl Stage A: 2-(p-chlorophenoxy) 2,2-dimethylacetate of 6'-(hydroxymethyl) 2'-pyridyl methyl There is introduced under agitation 17 grams of 2,6-pyridine bis-methanol into two liters of acetone. Then under agitation at a temperature of −3°C., 31.2 grams of the chloride of p-chlorophenoxyisobutyric acid is added. The reaction mixture is then maintained for 24 hours at ambient temperatures. The acetone solvent is then eliminated under reduced pressure and 50cm$^3$ of a solution saturated with sodium carbonate in 250cm$^3$ of methyl chloride is added. The organic phase is then washed, dried and the solvent removed under reduced pressure. On chromatography of the residual oil, there is obtained after concentration of the different fractions 18 grams of the 2-(p-chlorophenoxy) 2,2-dimethylacetate of 6'-(hydroxymethyl) 2'-pyridyl methyl.

Stage B: Hydrochloride of 2-(p-chlorophenoxy) 2,2-dimethylacetate of 6'-(N-methylaminocarbonyloxymethyl) 2'-pyridyl methyl There is introduced under agitation 10.8 grams of 2-(p-chlorophenoxy) 2,2-dimethylacetate of 6'-hydroxymethyl 2'-pyridyl methyl from Example I-A into 300cm$^3$ of anhydrous ether. There is then introduced 5.7 grams of methyl isocyanate. The mixture is maintained one night under agitation and then another 5.7 grams of methyl isocyanate is added and the mixture refluxed for 7 hours. The ether solvent and excess of methyl isocyanate are then removed under reduced pressure. The resulting residual oil is absorbed in isopropanol and a 6N hydrochloric acid solution in ethanol added to obtain an acid pH. The reaction mixture is maintained for 48 hours at about −5°C. The resulting solid is drained, washed and dried to recover products thus formed. There are obtained 13 grams of the hydrochloride of 2-(p-chlorophenoxy)-2,2-dimethylacetate of 6'-(N-methylaminocarbonyloxymethyl) 2'-pyridyl methyl, m.p. 110°C.

EXAMPLE II 2-(p-chlorophenoxy) 2,2-dimethylacetate of 6'-N-methylaminocarbonyloxymethyl) 2'-pyridyl methyl Four grams of the hydrochloride obtained in Example I are introduced with agitation into a mixture of 8cm$^3$ of dichloroethane and 8cm$^3$ of water. The resulting organic phase is decanted, washed with water, dried and treated with active carbon. Thereafter, the solvent is evaporated. The product obtained is crystalized in isopropyl ether to obtain 3.3 grams of 2-(p-chlorophenoxy) 2,2-dimethylacetate of 6'-(N-methylaminocarbonyloxymethyl) 2'-pyridyl methyl, m.p. 46°C.

EXAMPLE III

A pharmaceutical composition is prepared by compression of 1 gram of the active product as follows:

| | | |
|---|---|---|
| (1) | Hydrochloride of 2-(p-chlorophenoxy 2,2-dimethylacetate of 6'-(N-methylaminocarbonyloxymethyl) 2'-pyridyl methyl | 1 Gm |
| (2) | Excipient (talc, magnesium or wheat starch) | 1 Gm |

EXAMPLE IV

The following is a pharmacological study of the hydrochloride of 2-(p-chlorophenoxy) 2,2-dimethylacetate of 6'-(N-methylaminocarbonyloxymethyl) 2'-pyridyl methyl (Product A), and 2-(p-chlorophenoxy) 2,2-dimethylacetate of 6'-(N-methylaminocarbonyloxymethyl) 2'-pyridyl methyl (Product B):

1. Determination of the acute toxicity:

The acute toxicity is determined under lots of 10 mice weighing from 19 to 23 grams. The products A (from Example I-B) and B (from Example II), are administered in sesame oil in dosage amounts in the intraperitonial manner. The mean lethal dose, DL 50 has been determined by the methods of Litchfield and Wilcoxon (J. Pharmacol. Exp. Ther. 1949, 96, P. 133) after the mortality obtained after a week of observation.

The results obtained are as follows:
Product A: 1098 < DL 50 mg/Kg < 1281 (doses expressed as free base)
Product B: 915 < DL 50 mg/Kg < 1098

2. Determination of antibradykinine activity

The antibradykinine activity has been studied on the ilium of guinea pigs in vitro by the technique of preselecting the organ fragments and placing them in a tub, tank, vat or tray, containing a solution of Tyrode at about 37°C.

The product A in alcoholic solution is put into contact with the organ at concentrations of $0.1\gamma$ to $10\gamma$ per cm$^3$ of the tub. The bradykinine is then introduced at a concentration of $5.10^{-9}$ g. per cm$^3$ of the tub. The contractions obtained by the bradykinine are measured during and after administration of the product.

The results are expressed in percentage of reduction of the action of bradykinine:

$$\frac{\text{Contraction After bradykinine} - \text{Contraction After Product + Bradykinine}}{\text{Contraction After Bradykinine}} \times 100$$

| Product | Doses | | |
|---|---|---|---|
| | 0.1 γ/cm$^3$ | 1 γ/cm$^3$ | 10 γ/cm$^3$ |
| A % | 0 | 12 | 96 |

The active dose reduces by 50% the action of the bradykinine (DA$_{50}$) at 5γ/cm$^3$ of the tub.

Product A therefore exhibits very significant antibradykinine activity.

3. Determination of the hypolipemia activity:

a. Test carried out on normal animals:

The technique used is as follows:

The product A was administered to rats of the SPRAGUE DAWLEY strain by oral means during 5 consecutive hours. The day before killing, the animals were taken off food. The animals are sacrificed the 5th day and the cholesterol count is evaluated.

The results obtained, expressed as the difference between the serium count of cholesterol of the treated animals, and that of the control animals as a function of the doses of the Product A, are as follows:

| Product Studied | Doses | Variation of the Serial Cholesterol Count |
|---|---|---|
| Product A | 100 mg/kg | −15% |
|  | 200 mg/kg | −19% | b. Test carried out on the hyperlipemic animals:

The technique used is as follows:

The product A is administered to rats of the SPRAGUE DAWLEY strain rendered hyperlipemic by injection of the polymer of p-isooctylopolyoxyethylenephenol at the rate of 400 mg/kg using intraperitonial administration to the second day.

Product A is administered orally for three consecutive days (days 1, 2 and 3). The day before the sacrifice (day 3), the animals are taken off the food and the cholesterol count is evaluated on the fourth day.

The results are expressed as a function of the doses of Product A administered by the difference between the serial cholesterol count of the treated animals and that of the animals which have only received one administration of the polymer of p-isooctylpolyoxyethylenephenol.

| Product Studied | Doses | Variation of the Serial Cholesterol Count |
|---|---|---|
| Product A | 100 mg/kg | −18% |
|  | 200 mg/kg | −25% |

The product A therefore exhibits a very significant hypolipemic activity.

The invention has been described herein by reference to certain preferred embodiments but the invention is not to be considered as limited thereto.

What is claimed is:

1. The 2-(p-chlorophenoxy) 2,2-dimethylacetate of 6'-(N-methylaminocarbonyloxymethyl) 2'-pyridyl methyl of the formula:

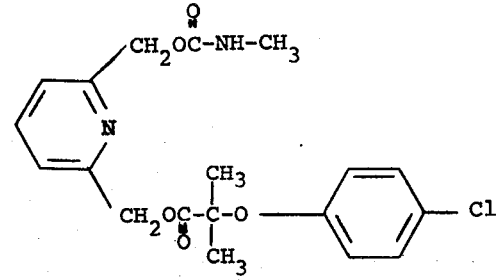

or a non-toxic acid addition salt thereof.

2. A compound according to claim 1 wherein the non-toxic acid addition salt is an acid addition salt of a mineral or organic acid selected from the group consisting of hydrochloric acid, hydrobromic acid, hydroiodic acid, nitric acid, sulfuric acid, phosphoric acid, acetic acid, maleic acid, fumaric acid, succinic acid, tartaric acid, citric acid, benzoic acid, alkylsulfonic acid and cyclohexylsulfamic acid.

3. A compound according to claim 1 which is the hydrochloride of 2-(p-chlorophenoxy) 2,2-dimethylacetate of 6'-(N-methylaminocarbonyloxymethyl) 2'-pyridyl methyl.

* * * * *